US006190713B1

(12) United States Patent
Babel

(10) Patent No.: US 6,190,713 B1
(45) Date of Patent: Feb. 20, 2001

(54) PROCESS AND A DEVICE FOR HEADSPACE FOAMING OF CONTAINERS FILLED WITH CARBONATED BEVERAGES

(76) Inventor: Olaf Babel, Freiheit 5, D-45527 Hattingen (DE)

( * ) Notice: Under 35 U.S.C. 154(b), the term of this patent shall be extended for 0 days.

(21) Appl. No.: 09/269,968

(22) PCT Filed: Oct. 10, 1997

(86) PCT No.: PCT/EP97/05587

§ 371 Date: Jun. 10, 1999

§ 102(e) Date: Jun. 10, 1999

(87) PCT Pub. No.: WO98/15491

PCT Pub. Date: Apr. 16, 1998

(30) Foreign Application Priority Data

Oct. 10, 1996 (EP) .................... 96116250

(51) Int. Cl.[7] .................... A01K 43/00; C12G 1/06; G01N 33/02

(52) U.S. Cl. .................... 426/232; 426/329; 426/330.3; 426/395; 426/397; 426/477

(58) Field of Search .................... 426/107, 232, 426/239, 237, 329, 330.3, 569, 395, 390, 397; 99/477

(56) References Cited

U.S. PATENT DOCUMENTS

| | | | |
|---|---|---|---|
| 5,473,161 | * 12/1995 | Nix et al. | 250/343 |
| 5,683,732 | * 11/1997 | Baxter et al. | 926/115 |

FOREIGN PATENT DOCUMENTS

| | | |
|---|---|---|
| 19 61 876 | 12/1969 | (DE) . |
| 91 16 815 U 1 | 10/1991 | (DE) . |
| 44 15 852A | 11/1995 | (DE) . |
| 2 026 689A | 9/1970 | (FR) . |
| 63-104620 | 5/1988 | (JP) . |

* cited by examiner

*Primary Examiner*—Nina Bhat
(74) *Attorney, Agent, or Firm*—Tilton, Fallon, Lungmus & Chestnut

(57) ABSTRACT

A process for the foaming of the headspace of containers filled with carbonated beverages, wherein, after the filling of the beverages into the containers, the containers are transferred to a foaming area, in which an electromagnetic beam, preferably a laser beam, is irradiated in a controlled way into the headspace of the container which is not filled with the beverage, whereby, due to the resultant foaming, the gas volume in the headspace is displaced from it, and the containers are subsequently sealed, as well as to a device for carrying out the process.

13 Claims, 2 Drawing Sheets

PROCESS AND A DEVICE FOR HEADSPACE FOAMING OF CONTAINERS FILLED WITH CARBONATED BEVERAGES

This application is a 35 U.S.C. 371 national stage application based on PCT/EP97/05587 filed on Oct. 10, 1997.

FIELD OF THE INVENTION

The invention relates to a process for headspace foaming of containers filled with carbonated beverages, in which the beverage is foamed in the container after filling so that the volume previously contained in the headspace is displaced from it due to the ascending foam, and a device for carrying out this process.

BACKGROUND OF THE INVENTION

In bottling plants, beverages are filled into containers in such a way that a residual gas volume remains in the headspace of the containers. This residual volume is at first filled with carbon dioxide in the case of beverages containing $CO_2$. Since the containers are exposed to ambient air during transfer form the bottling station to the sealing station, there is a risk of oxygen entering the headspace during this transfer, which promotes germ formation in such beverages and thus greatly reduces their storage stability.

For the afore-mentioned reason, beverages are conventionally foamed during transfer from the bottling station to the sealing station by introducing a gaseous or liquid medium into the headspace onto the surface of the beverage so that the resultant foam expels the gas volume, and thus also the oxygen that has entered, from the headspace. Thus, the oxygen content in the headspace will be reduced at the moment the container is sealed.

One example of such a foaming device is disclosed in German Utility Model No. 91 16 815 U1. A jet of liquid, here in particular water, is introduced into the headspace of the filled containers at a pressure of 40 bar by means of the device described therein. The pulse of the water jet can be regulated.

It is in particular disadvantageous in such process and devices according to the prior art that after the high-pressure water injection the beverage foam has relatively large pores so that, despite large overfoam volumes (2 to 5 ml/container), the average oxygen values that can be achieved in the headspace are not better than 0.018 to 0.12 mg per liter. The disadvantageously large overfoaming results in a high waste water pollutant load and thus substantial liquid waste disposal costs; also, the large overfoam volumes are equivalent to net beverages losses which, of course, are expensive per se.

A further main disadvantage of this known foaming process resides in the fact that water, and thus foreign media, is injected into the beverage, thereby diluting it. There is danger of germs being injected into the beverage together with the water, while, to avoid this danger, special equipment for preparing germ-free water must be provided.

SUMMARY OF THE INVENTION

The object of the present invention is to create a method and a device for headspace foaming of containers filled with carbonated beverages, which overcome the aforementioned disadvantages of the prior art. In particular, the invention is intended to achieve a good storage stability of the contained beverages and very low foaming losses.

The advantage of foaming the beverage according to the invention is first that the foam ascending from electromagnetic beam foaming has much finer pores than, for instance, foam resulting from water injection, and thus becomes substantially more gas-tight. The amount of oxygen remaining in the headspace after foaming with an electromagnetic beam is very low, and in a range that conventional high-pressure injection systems with comparable overfoaming losses cannot even approach.

Another advantage is that the microporous foam arising from the irradiation with a controlled electromagnetic beam can be regulated very well with regard to the resultant foam quantity and therefore foaming losses can be minimized. Thus, the overfoam volumes, which are expensive and waste-water polluting per se, can be greatly reduced.

A further advantage of the foaming according to the invention resides in the fact that special plant technologies for preparing germ-free water are no longer required since, as a matter of course, water is not used as a foaming agent. As a further result of the fact that the introduction of water can be dispensed with is that the beverage no longer experiences dilution or contamination with residual germs in the water.

The electromagnetic beam may be, for example a micro wave beam or the like. According to a preferred embodiment of the invention, the electromagnetic beam comprises a laser beam.

According to a preferred embodiment of the present invention, the containers pass along a bottling conveyor, a transfer conveyor and a sealing conveyor, with the point of foaming by means of laser irradiation being located immediately upstream of the point of sealing of the containers. According to such a development, the foaming of the beverage is carried out shortly before the sealing of the containers, i.e. there is little time for the oxygen-containing ambient air to enter the headspace after the foam has displaced the gas therein.

In accordance with one embodiment of the present invention the laser beam is radiated into the headspace in a pulsed fashion, while it may preferably be triggered by a triggering means such as an ultrasonic switch or a light barrier at a triggering rate adapted to the speed of the containers that pass through. As an alternative to triggering by external triggering means, the laser beam may be pulsed per se.

However, the laser beam may, alternatively, also be radiated into the headspace in a continuous fashion.

The laser beam radiated onto the surface of the beverage may be adjusted in its intensity, pulse shape, length and/or frequency; according to the requirements of the specific application.

According to a further embodiment of the invention, the level of foam in the headspace is measured or detected, respectively, by measuring means and the intensity, pulse shape, length and/or frequency are adjusted dependent on the detected level.

By means of controlling devices as usually employed in laser technology the following parameters for the laser radiation may be set for a preferred embodiment of the invention.

The average power of the laser beam irradiated onto the surface of the beverage may be adjusted in the range of about 10 to 20000 W; the frequency of the laser beam may be adjusted in the range of about 5 to about 2000 Hz, and the shutter opening time should be in the range of 5 ms to 2000 ms.

The foaming of the beverage is induced by the energy of the laser beam. Since different beverages also foam differently, the power of the laser beam irradiated into the headspace can in each case be adjusted so accurately that foaming losses are minimized while, at the same time, the greatest possible amount of oxygen is expelled.

Advantageously, the vicinity of the laser beam radiation point may be surrounded by a haze of an inert gas, provided by a corresponding apparatus, in order to avoid the entry of ambient air into the headspace.

The device according to the invention preferably has a laser beam emitter comprising a $CO_2$ laser with a maximum performance of 10 to 20000 W, a duty cycle of 5 to 100%, an optical guiding system for the laser beam, and a focusing means with a lens having a diameter of about 3.81 cm (1.5 in.) and focal point diameter of 300 to 500 $\mu$m.

BRIEF DESCRIPTION OF THE DRAWING

The invention is explained in the following referring to the appended Figures.

FIG. 1 shows an elevation of an embodiment of a device according to the invention for headspace inertization. The foaming means of this device is designated in general with the reference numeral 10. It comprises a $CO_2$ laser 15 which is firmly anchored to the floor next to a transfer conveyor 33 indicated in dash-dotted lines. The transfer conveyor 33 conveys containers 18, here bottles, already filled with beverage from a bottling conveyor 31 to a sealing conveyor 32 (cf. FIG. 3).

Figure 1:
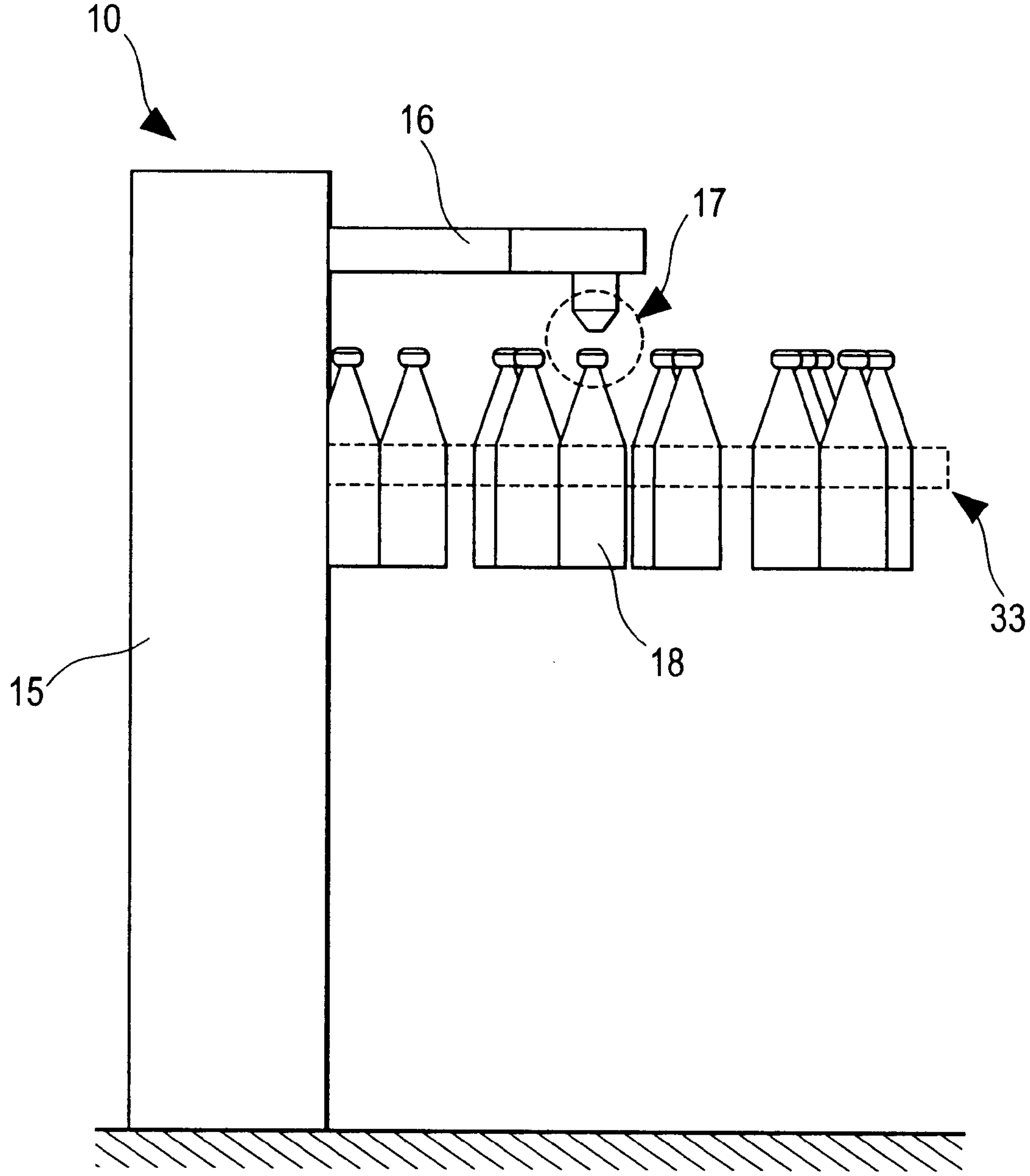
FIG. 1 shows an elevation of a device according to the invention for headspace inertization.

The $CO_2$ laser 15 provides a laser beam which is directed into an optical guiding system 16 for the laser beam. This system 16 is designed as an arm spanning the distance between the $CO_2$ laser 15, the focus means 17 being placed directly above the mouth of the bottle 18 to be processed.

The laser beam irradiated onto the surface of the beverage has a power of about 10 to about 20000 W, the frequency of the laser beam being adjusted to about 5 to about 2000 Hz, and the shutter opening time being about 5 ms to 2000 ms. The employed $CO_2$ laser shows an average performance of about 10 to about 20000 W and has a duty cycle of about 5 to 100%.

The above variable parameter are set by known control devices for laser beam technology and adjusted in such a way that, in any case, a suitable laser beam with a predetermined power is injected for a specific type of beverage with a predetermined carbonization and/or a predetermined $CO_2$ contents which effects a foaming in the beverage, but does not result in high foaming losses. Thus, foaming is induced in a proportional relationship with the power of the laser beam. In the optimum case, the laser beam is radiated onto a black surface.

The foaming of the beverage by a laser results in a highly microporous foam which displaces the gas volume contained in the bottle 18 up to then due to its ascension in the headspace of the containers 18. Because of its microporosity, the resultant foam is highly gas-tight and effects a type of plug flow in the container neck. Therefore, only a very small amount of the original gas volume remains in the headspace, the gas tightness of the microporous foam alone prevents air from the environment from entering the headspace.

As a result of this process, the oxygen content in the headspace is at a very low value when the containers 18 are sealed, a result which conventional high pressure water injections in which large-pore foam is formed can not achieve. With such a small amount of oxygen in the headspace, the risk of germ formation is minimized. The storage stability of the filled beverage is greatly improved. Due to the exact adjustability of the parameters of the laser beam, an exactly controllable foaming takes place, and overfoaming losses are largely prevented so that high pollutant loads in the waste water can also be prevented.

Figure 2:
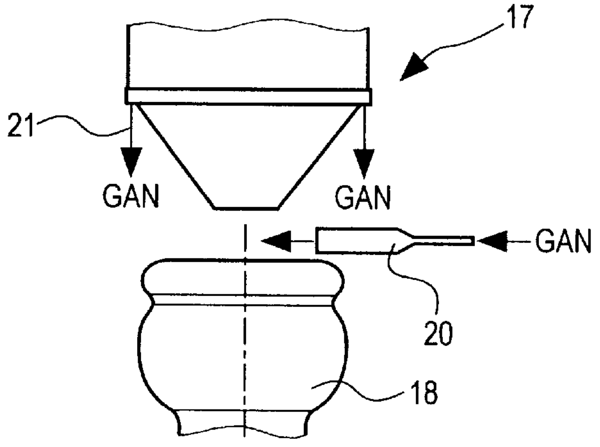
FIG. 2 shows a detail of FIG. 1.

In FIG. 2 the focus means 17 is shown. It may be seen that the lens center is positioned at a short distance directly above the center of the bottle mouth such that the laser beam emitted therefrom directly hits the surface of the beverage without being deflected by any portion of the bottle neck.

FIG. 2 further shows how the vicinity of the bottle mouth may be surrounded with a haze of gaseous nitrogen (GAN). Two streams of gaseous nitrogen are employed, namely one annular vertical stream 21 which may be supplied by an annular nozzle 20 surrounding the focus means 17, and a horizontal stream supplied by a nozzle 20. The vertical GAN stream prevents air from entering the bottle neck, while the horizontal stream and the vertical stream prevent foam ascending in the headspace of the bottle 18 from approaching the focus means and thereby contaminating it.

Figure 3:
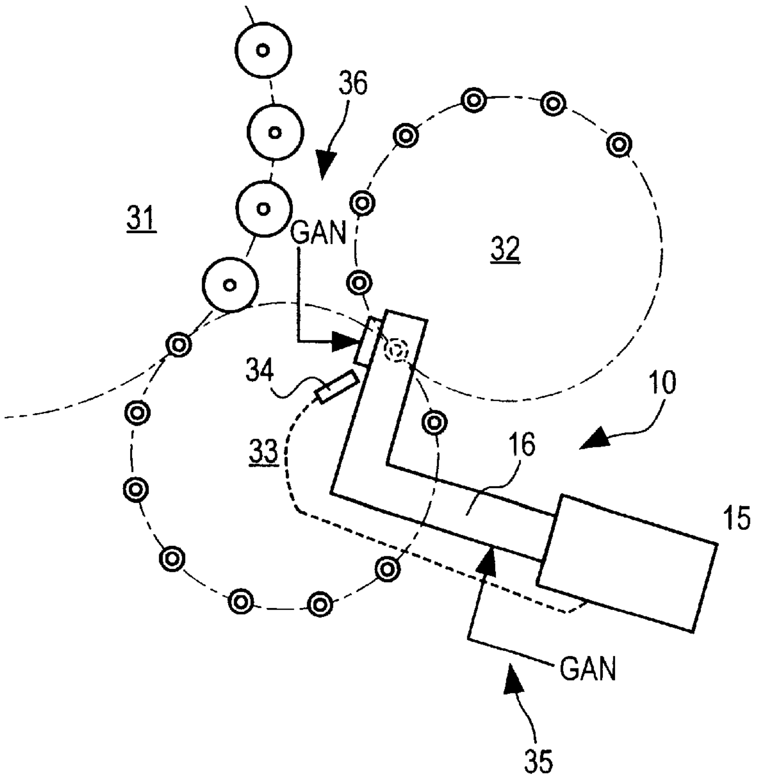
FIG. 3 shows a top view of a headspace inertization means according to the invention and its arrangement with respect to a bottling conveyor, a transfer conveyor and a sealing conveyor for containers, here bottles.

The supply means for the GAN streams are described in FIG. 3 which shows a top view of the headspace inertization means according to the invention. The arrangement of the foaming means 10 with the $CO_2$ laser 15, the arm 16 of the optical guiding system for the laser beam, and the focus means 17 in relation to the conveying facilities for the containers 18 is apparent from this view. Filled containers 18 are delivered by a bottling conveyor 31 that rotates clockwise, and is partially shown at the lefthand side, to a transfer conveyor 33 which rotates counterclockwise. Just before the sealing of the bottles 18 in the sealing conveyor 32, the laser beam is radiated into a container 18. This irradiation takes place just prior to the sealing of the container 18 so that as little ambient air as possible can enter the headspaces of the containers 18 before they are sealed.

Upon irradiation by the laser beam the beverage liquid contained in the bottles 18 foams so that the gas in the headspace is expelled and no ambient air can enter the headspace of the containers 18 until they are sealed.

Supply means 35 and 36 for the GAN hazing streams are also shown in FIG. 3. They may comprise pipes with valves incorporated, leading from a GAN reservoir to the annular nozzle providing a GAN stream 21 (FIG. 2) or to the nozzle 20 (FIG. 2) providing the horizontal GAN stream.

The supply means 35 comprises a pipe which leads through the arm 16 to the focus means at the radiation point.

A sensoring means 34 in connection with the triggering control of the laser 15 is arranged near the radiation point. This sensoring means 34 supplies information about the frequency of the arriving bottles 18 so that the laser 15 may be triggered exactly in correspondence with said frequency.

Although the invention has been described by means of an embodiment so far with regard to foaming of beverage in bottles, it is understood that the process and the device according to the invention can also be used for headspace foaming of other containers, e.g. cans, etc. and for the foaming of various beverages, e.g. beer, soft drinks, etc., in particular carbonated beverages.

What is claimed is:

1. A process for the foaming of the headspace of containers (18) filled up to said headspace with carbonated beverages, comprising the steps of:

a) transferring the containers, after filling beverages into the containers (18), to a foaming means (10);

b) radiating in a controlled fashion an electro-magnetic beam that comprises a laser beam, and pulsing said laser beam by triggering means in the form of an ultrasonic switch, while directing said beam into the headspace of the container (18) to cause controlled foaming of said beverage;

c) due to the resultant foaming, displacing the gas volume contained in the headspace from said headspace; and d) sealing the containers (18).

2. A process for the foaming of the headspace of containers (18) filled up to said headspace with carbonated beverages, comprising the steps of:

a) transferring the containers, after filling beverages into the containers (18), to a foaming means (10);

b) radiating in a controlled fashion an electro-magnetic beam that comprises a laser beam, and pulsing said laser beam by triggering means in the form of a light barrier, while directing said beam into the headspace of the container (18) to cause controlled foaming of said beverage;

c) due to the resultant foaming, displacing the gas volume contained in the headspace from said headspace; and d) sealing the containers (18).

3. A process according to claim 1 or 2, and the step of adjusting said laser beam as radiated onto the surface of the beverage for any of its intensity, pulse shape, length and frequency.

4. A process according to claim 3, and the steps of: a) measuring the level of foam in the headspace, and b) adjusting any of the intensity, pulse shape, length and frequency of the laser beam dependent on the measured level of foam.

5. A process according to claim 3, and the steps of: adjusting the average power of the laser beam as irradiated onto the surface of the beverage in the range of about 10 to about 20000 W, adjusting the frequency of the laser beam in the range of about 5 to about 20000 Hz, and adjusting the shutter opening time in the range of about 5 to about 20000 ms.

6. A process according to claim 3, in which there is the step of surrounding the vicinity of the laser beam irradiation point by a haze of an inert gas in order to avoid the entry of ambient air into the headspace and contamination of the focus means.

7. A device for foaming of the headspace of containers (18) filled up to said headspace with carbonate beverages, comprising in combination:

a) filling means (31) for filling the beverage into the containers (18), b) foaming means (10) to which said containers (18) are transferred after having been filled by means of which the gas volume previously present in the headspace of said containers (18) is displace due to the resultant foaming, c) sealing means for said containers (18), d) said foaming means comprising a laser beam emitter (15, 16, 17) for the controlled irradiation of a laser beam into said headspace of said containers (18), including triggering means in the form of an ultrasonic switch for the controlled pulsing of said laser.

8. A device for foaming of the headspace of containers (18) filled up to said headspace with carbonate beverages, comprising in combination:

a) filling means (31) for filling the beverage into the containers (18), b) foaming means (10) to which said containers (18) are transferred after having been filled by means of which the gas volume previously present in the headspace of said containers (18) is displace due to the resultant foaming, c) sealing means for said containers (18), d) said foaming means comprising a laser beam emitter (15, 16, 17) for the controlled irradiation of a laser beam into said headspace of said containers (18), including triggering means in the form of a light barrier for the controlled pulsing of said laser.

9. A device according to claim 7 or 8, and a controlling means adjusting said laser beam in any of its intensity, pulse shape, length and frequency.

10. A device according to claim 9, and means for measuring the level of foam in said headspace whereby any of the intensity, pulse shape, length and frequency of said laser beam are adjusted dependent on the measured level of foam.

11. A device according to claim 9, wherein said controlling means are adjusting the average power of said laser beam as irradiated onto the surface of the beverage in the range of about 10 to about 20000 W, adjusting the frequency of the laser beam in the range of about 5 to about 20000 Hz, and adjusting the shutter opening time in the range of about 5 to about 20000 ms.

12. A device according to claim 7 or 8, wherein said laser beam emitter comprises a $CO_2$ laser (15) with an average performance of 10 to 20000 W, a duty cycle of 5 to 100%, an optical guiding system (16) for said laser beam, and a focus means (17) with a lens having a diameter of about 3.81 cm (1.5 in.) and a focal point diameter in the range of from 300 to 500 $\mu$m.

13. A device according to claim 7 or 8, and a hazing means surrounding the vicinity of the laser beam radiation point by a haze of an inert gas in order to avoid the entry of ambient air into said headspace and contamination of the focus means.

* * * * *

UNITED STATES PATENT AND TRADEMARK OFFICE

CERTIFICATE OF CORRECTION

PATENT NO. : 6,190,713 B1
DATED : February 20, 2001
INVENTOR(S) : Olaf Babel

It is certified that error appears in the above-identified patent and that said Letters Patent is hereby corrected as shown below:

Column 6,
Line 2, "displaced" should be -- displace --.
Line 19, "displaced" should be -- displace --.

Signed and Sealed this

Fifth Day of March, 2002

Attest:

JAMES E. ROGAN

*Attesting Officer* *Director of the United States Patent and Trademark Office*